United States Patent [19]

Barberet et al.

[11] Patent Number: Plant 5,434

[45] Date of Patent: Apr. 9, 1985

[54] CARNATION NAMED LONBLITEC

[75] Inventors: Nicole Barberet; Yves Ducloux, both of Antibes, France

[73] Assignee: Laboratoire de Physiologie Vegetale de La Londe, Antibes, France

[21] Appl. No.: 516,565

[22] Filed: Jul. 25, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation cultivar particularly distinguished by its small, substantially pure white blossoms which are borne on upright, straight peduncles carried by a strong, tall, flowering stem having rather abundant foliage and a vigorous growth habit which is rather resistant to *Fusarium oxysporum.*

1 Drawing Figure

BACKGROUND OF THE NEW PLANT

Our new spray carnation cultivar is the result of breeding efforts carried on by us at La Londe, Les Maures, France, since 1978 with the object of developing a white carnation with good quality of flower stem and plant growth habit and which is particularly resistant to *Fusarium oxysporum.* This new plant originated as a seedling produced by our crossing of selected and individually identified plants growing among our stock of spray carnations maintained at La Londe for breeding purposes and this particular seedling was selected by us for propagation and test because of its pure white blossoms which are produced profusely on a tall, flowering stem having abundant foliage and an apparent very strong resistance to *Fusarium oxysporum.* This discovery plant was reproduced by us at La Londe, by means of cuttings, with such a favorable result with respect to retention of the novel characteristics of the parent plant that we continued such propagation through several successive generations and thereby determined that the novel and distinctive characteristics of the discovery plant are fully retained from generation to generation and appear to be firmly fixed.

DESCRIPTION OF THE DRAWING

Our new spray carnation is illustrated by the accompanying photographic drawing which shows, in full color, the upper portion of a typical flowering stem with buds and flowers in various stages of opening, the color rendition being as nearly true as is reasonably possible to obtain by conventional photographic procedures.

DESCRIPTION OF THE NEW PLANT

The following is a detailed description of our new spray carnation discovery based upon observations of greenhouse grown plants at La Londe, France, in the Spring of 1983, the color descriptions being specified according to The R.H.S. Colour Chart published by The Royal Horticultural Society of London, England.

THE PLANT

Origin: Seedling

Parentage:

*Seed parent.*—Stock Plant No. 73 M P 3.

*Pollen parent.*—Stock Plant No. 9 M B 3. These unnamed varieties are individually identified in our permanent records and are maintained in our spray carnation collection for breeding purposes at La Londe, France.

Classification:

*Botanic.*—*Dianthus caryophyllus.*

*Commercial.*—Spray Carnation.

Form: Tall, erect bush with at least four stems emitted near the ground.

Height: About 95 cm. in average at eight months.

Main stem:

*Length.*—Less than 15 cm. due to pinching.

Branching character: Well branched on all stems.

Growth habit: Vigorous and upright with good strength.

Foliage:

Quantity.—Rather abundant.

*Number of leaves.*—At least 120.

*Leaf size.*—About 12 cm. long and 8 mm. wide, in average at the seventh node.

*Leaf shape.*—Linear with rolled margins.

*Texture.*—Leathery.

*Color.*—Upper side — 189A. Under side — 189A.

*Ribs and veins.*—Hardly noticeable.

*Rachis.*—Hardly noticeable.

THE BUD

Size: Medium.

*Diameter.*—About 1.1 cm. in average.

*Length.*—About 2.6 cm. in average.

Shape: Long ovoid.

Rate of opening: Normal for carnations.

Color of petals:

*When sepals first divide.*—White, R.H.S. 155D.

*When petals begin to unfurl.*—White, R.H.S. 155D.

Sepals:

*Number.*—Five.

*Shape.*—Joined at the lower part with the upper part of acute form and sharply pointed at the apex. Sepals are hooded over the bud and stand up when the flowers open.

*Color.*—Inside — Greenish white.Outside — R.H.S. 137D and 144B.

*Striae.*—Longitudinal.

Calyx:

*Size.*—Medium.

*Shape.*—Long, generally cylindrical and slightly bell-shaped at its upper portion.

*Splitting.*—The calyx does not split.
*Aspect.*—Smooth.

Flower stem:
*Length.*—About 65 cm.
*Character.*—Erect and rather thin.
*Color.*—R.H.S. 189A.

THE FLOWER

Blooming habit: Recurrent, blooming profusely during midseason of Spring and Fall.

Size of bloom: Small.
*Diameter.*—About 5.7 cm. in average.
*Depth.*—About 5.3 cm. in average.

Borne: In cluster.

Shape:
*When bloom first opens.*—High centered.
*When bloom matures.*—Dome-shaped.

Petalage:
*Number of petals.*—About 35 in average.
*Arrangement.*—Imbricated.
*Form.*—Fan-shaped with round edges, the outer edge being finely serrated.
*Texture.*—Soft.
*Appearance.*—Satiny.
*Color.*—Outer Petal — R.H.S. 155D. Base — Greenish. Reverse side — R.H.S. 155D. Inside Petal: Body — R.H.S. 155D. Base — Greenish. Reverse side — R.H.S. 155D.

Petaloids:
*Number.*—Less than 7.
*Size.*—Smaller than the petals.
*Color.*—The same as the petals.

Flower stem:
*Length.*—About 65 cm.

*Character.*—Upright and of good strength.
*Color.*—R.H.S. 189A.

Fragrance: Strong.

Persistence: The flowers hang on and dry.

Lasting quality:
*As a cut flower.*—At least ten days in vase keeping.

Disease resistance: Rather resistant to *Fusarium oxysporum* as observed INRA, Antibes, Alpes-Maritimes, France.

REPRODUCTIVE ORGANS

Stamens:
*Number.*—4 to 12.
*Arrangement.*—Encircling the pistils.
*Anthers.*—Size: Less than 4 mm. Color: Whitish.
*Filaments.*—Color — Whitish.

Pistils:
*Number.*—Two.
*Styles.*—Color — White.
*Stigmas.*—Color — White.

This new variety of spray carnation most resembles "White Elegance" but differs by having a longer stem, a more branched spray, and a spotless white flower. Furthermore, this new variety differs from "White Elegance" by its resistance to *Fusarium oxysporum.*

We claim:

1. A new and distinct spray carnation cultivar, substantially as herein shown and described, characterized by the very white color of its small blooms which are produced profusely on tall, straight and strong flowering stems which have a vigorous and upright growth habit with abundant foliage and resistance to *Fusarium oxysporum.*

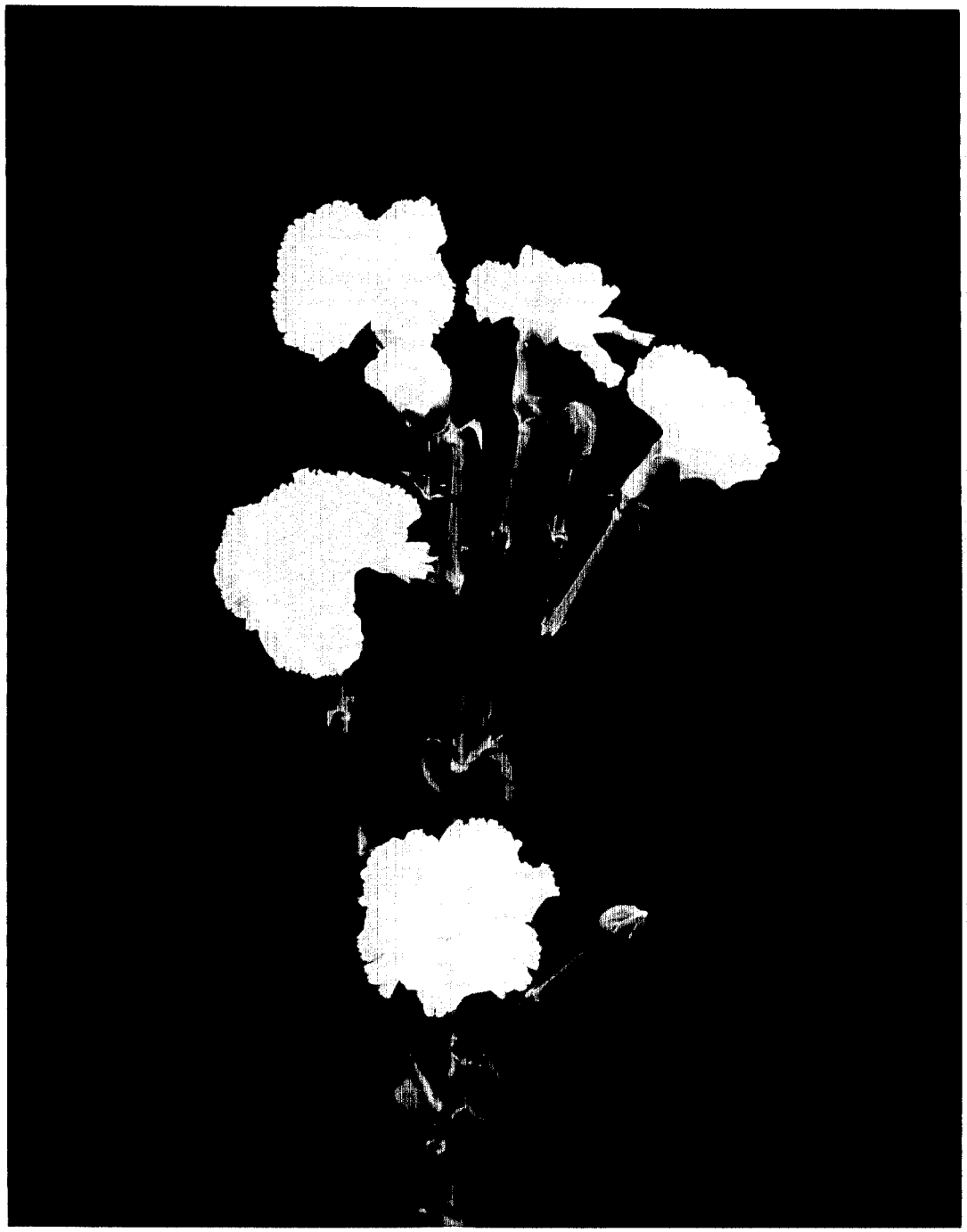

* * * * *